United States Patent [19]

Miyano et al.

[11] 3,935,221
[45] Jan. 27, 1976

[54] SUBSTITUTED FUSARIC ACID DERIVATIVES

[75] Inventors: Tetsuji Miyano; Kunio Suzuki; Hiroshi Fukatsu, all of Nagoya, Japan

[73] Assignee: Banyu Pharmaceutical Co., Ltd., Nagoya, Japan

[22] Filed: Apr. 17, 1974

[21] Appl. No.: 461,595

Related U.S. Application Data

[63] Continuation-in-part of Ser. No. 257,834, May 30, 1972, Pat. No. 3,835,146.

[30] Foreign Application Priority Data

May 28, 1971  Japan.............................. 46-36220
Oct. 1, 1971  Japan.............................. 46-76237

[52] U.S. Cl... 260/295 AM; 260/270 R; 260/295 R; 260/295 S; 424/266
[51] Int. Cl.²..................................... C07D 213/56
[58] Field of Search................. 260/295 AM, 295 R

[56] References Cited
UNITED STATES PATENTS 3,519,717  7/1970  Symchowicz et al............. 424/266

FOREIGN PATENTS OR APPLICATIONS 1,219,176  1/1971  United Kingdom......... 260/295 AM

*Primary Examiner*—Norman A. Drezin
*Attorney, Agent, or Firm*—Oblon, Fisher, Spivak, McClelland & Maier

[57] ABSTRACT

Halo-fusaric acid amides having the formula

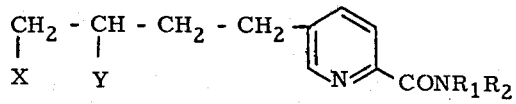

wherein X represents halogen or hydrogen, Y represents halogen and $R_1$ and $R_2$ are same or different and represent hydrogen or a lower alkyl group ($C_{1-4}$) which are characterized by significant activity in the treatment of hypertension.

2 Claims, No Drawings

SUBSTITUTED FUSARIC ACID DERIVATIVES

CROSS REFERENCE TO RELATED APPLICATIONS

This application is a Continuation-In-Part of application Ser. No. 257,834, filed May 30, 1972 now U.S. Pat. No. 3,835,146.

BACKGROUND OF THE INVENTION

1. Field of the Invention:

This invention relates to novel halo-fusaric acid amides and to a method of preparing said compounds. This invention also relates to a method of using said novel halo-fusaric acid amides for the treatment of hypertension.

2. Description of the Prior Art:

Fusaric acid is known to be a metabolism product produced by microorganisms, particularly vegetable germs. It has recently been discovered that fusaric acid will inhibit the production of dopamine-$\beta$-hydroxylase, and hence might be useful in pharmacological preparations, except that it is quite high in toxicity. It would be quite desirable, therefore, to provide related derivatives of fusaric acid which are likewise characterized by dopamine-$\beta$-hydroxylase inhibiting activity, but which have a reduced toxicity level.

SUMMARY OF THE INVENTION

Accordingly, it is one object of this invention to provide halo-fusaric acid amides. It is still another object of this invention to provide a process of using said fusaric acid to reduce the levels of dopamine-$\beta$-hydroxylase and for the treatment of hypertension. These and other objects, as will hereinafter become more readily apparent, have been attained by the provision of halo-fusaric acid amides of the formula:

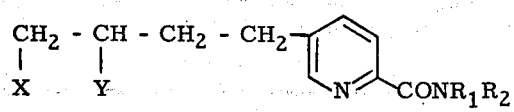

wherein X represents halogen or hydrogen, Y represents halogen, and $R_1$ and $R_2$ are same or different and represent hydrogen or a lower alkyl group ($C_{1-4}$).

DETAILED DESCRIPTION OF THE PREFERRED EMBODIMENTS

The halo-fusaric acid amides of this invention have the formula:

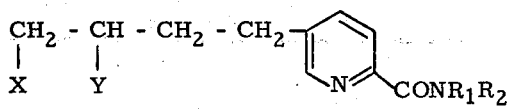

wherein X represents hydrogen or halogen atom; and Y represents a halogen atom; $R_1$ and $R_2$ are same or different and represent hydrogen or a lower alkyl group ($C_{1-4}$). Representative of X and Y are hydrogen, chlorine, bromine, and iodine atom. Representative of $R_1$ and $R_2$ are hydrogen, methyl, ethyl, propyl and butyl. Accordingly, —$NR_1R_2$ groups are amino, monomethylamino, dimethylamino, monoethylamino, diethylamino, monopropylamino, dipropylamino, methylethylamino, methylpropylamino and ethylpropylamino group, etc. The typical compounds of this invention are 10,11-dibromofusaric acid amide,
10,11-dichlorofusaric acid amide,
10-monobromofusaric acid amide,
10,11-dibromofusaric acid monomethylamide,
10,11-dichlorofusaric acid monomethylamide,
10,11-dibromofusaric acid dimethylamide,
10,11-dichlorofusaric acid dimethylamide.

10,11-Dihalo-fusaric acid can be prepared by dissolving dehydrofusaric acid in an inert organic solvent, e.g., chloroform, and ether, cooling and admixing with a halogen to provide an addition reaction. The 10,11-dihalo-fusaric acid product can then be purified by conventional purification procedures, such as recrystallization or silica chromatography to yield purified crystals. Typical of the 10,11-dihalo-fusaric acid produced herein is 10,11-dibromo-fusaric acid, which is characterized as colorless needle-like crystals having a melting point of 105° – 106°C, and is soluble in alcohol, chloroform, benzene, ethylacetate, and hot water. It is insoluble in cold water and petroleum ether, and yields a positive test result to Beilstein reagent. Elementary Analysis shows that the compound is: C : 35.6%, H: 3.33%, N: 4.30%, and Br: 46.92%(calculated value of $C_{10}H_{11}O_2N.Br_2$ C: 35.64%, H: 3.29%, N: 4.16%, Br: 47.42%). The ultraviolet absorption spectrum of the compound is $\lambda$max in methanol 269 m$\mu$ and $E_{1cm}^{1\%}$159 (the ultraviolet absorption spectrum of fusaric acid is $\lambda$max in methanol 269 m$\mu$ $E_{1cm}^{1\%}$310.)

The nuclear magnetic resonance spectrum (CDCl$_3$) of this compound is as follows:

| | |
|---|---|
| $\delta$ 2.0 – 2.7, 2H, multiplet, | (-CHBr-CH$_2$-CH$_2$-); |
| $\delta$ 2.7 – 3.2, 2H, multiplet, | (-CH$_2$-CH$_2$-); |
| $\delta$ 3.4 – 4.3, 3H, multiplet, | (CH$_2$Br-CHBr-CH$_2$-); |
| $\delta$ 7.7 – 7.9, 1H, doublet, | (aromatic H̲); |
| $\delta$ 8.05 – 8.25, 1H, doublet, | (aromatic H̲); |
| $\delta$ 8.65, 1H, singlet (broad), | (aromatic H̲); |
| $\delta$ 10.0, 1H, singlet | (Carboxylic H̲). |

In this invention, 10-monohalo-fusaric acid can be prepared by dissolving dehydrofusaric acid in water or other suitable organic solvent, if necessary, together with a suitable reagent for generating hydrogen halide. Hydrogen halide is then introduced or generated to effect the addition reaction. 10-bromo-fusaric acid prepared in accordance with the process of this invention is characterized as colorless needle-like crystals having a melting point of 112° – 113°C, and is soluble in alcohol, chloroform, acetone, benzene, ethylacetate, and is soluble in hot water but difficulty soluble in cold water. It is insoluble in n-hexane, petroleum ether, and proves positive with Beilstein reagent. The halo-fusaric halide can be prepared by reacting halogenating agent such as thionylchloride, hydrochloride with halo-fusaric acid in a solvent. The solvent can be inert solvent or halogenating agent such as thionyl chloride. The ahlo-fusaric acid amides of the invention can be prepared from the halo-fusaric halide in a solvent by introducing ammonia gas or adding methylamine, dimethylamine, ethylamine, diethylamine, etc.. The halogenating agents used for preparing halo-fusaric halide can be thionylchloride, hydrochloride, phosphorus pentachloride and phosphorus oxychloride. The thionylchloride can be used without a solvent, however, it is usual to carry out the halogenation of halo-fusaric acid in a solvent such as chloroform, benzene, etc.. The halo-fusaric halide reacts with ammonia or a lower alkylamine in a solvent such as chloroform, benzene, etc.. The ahlo-fusaric acid amide can be prepared from halo-fusaric acid ester by reacting it with an alkylamine. The halo-fusaric acid ester can be prepared by reacting halo-fusaric acid with an alcohol in the presence of chlorine gas. The details of the preparation of the halo-fusaric acid can be understood from the description of the examples. The halo-fusaric acid amides of the invention are characterized by a significant anti-hypertensive effects and low toxicity. The followings are test results of anti-hypertensive effects and toxicities of the typical halo-fusaric acid amides of the invention. The anti-hypertensive effects of dibromo, monobromo, dichloro and monochloro fusaric acid amide, monomethylamide, dimethylamide were compared with those of dibromofusaric acid and fusaric acid. Blood pressure of spontaneously hypertensive rats (SHR) derived from the colony of SHR produced by selective inbreeding of a strain of Wistar rats (Okamoto and Aoki, Jap. Circul. J. 27:282–293, 1963) was measured indirectly in unanaesthesized rats plethysmographically (Williams et al, J. Clin. Invest. 18:373–376, 1939). Thirty percent depression of systolic blood pressure was defined to be significant and effective change. Table 1 showed $LD_{50}$ and $ED_{50}$ for antihypertensive action of the drugs. $LD_{50}$ of each drug was obtained using male mice (DBA). It is clear that dibromofusaric acid amide is the least toxic and the most effective drug for hypertension.

[EXAMPLE 1]

5-(3,4-Dibromobutyl)picolinamide→ 10,11-dibromofusaric acid amide 20 g of 5-(3,4-dibromobutyl)picolinic acid was added to 15 ml of thionyl chloride and resulting solution was kept to warm at 50°C for one-half hour. Reaction mixture was evaporated in reduced pressure and resulting oily residue was dissolved in chloroform 100 ml. Through the solution dry ammonia gas was passed for five minutes with cooling. White precipitate was removed by filtration and washed with chloroform. Filtrate and washings are combined and evaporated in reduced pressure. Resulting solid was crystallized from benzene to give 10.2 g of the pure product as platelets.

| | |
|---|---|
| m.p. | 138.5 – 140.5°C |
| Anal.; | $C_{10}H_{12}ON_2Br_2$ |
| | calc.; C 35.74, H 3.60, N 8.34, Br 47.56 |
| | found; C 35.98, H 3.88, N 8.51, Br 47.15 |
| IR(KBr); | 1680, 1660 cm$^{-1}$ |
| UV; | $\lambda_{max.}^{MeOH}$ 269 nm ($\epsilon$ 5400) |
| TLC; | Rf 0.72 (Silicagel; chloroform-methanol - acetic acid = 45:4:1) |
| Solubility; | Soluble in alcohol, acetone, benzene, chloroform Insoluble in water, ether. |

[EXAMPLE 2]

5-(3,4-Dibromobutyl)picolinamide→

10 g of 5-(3,4-dibromobutyl)picolinic acid was dissolved in 200 ml of ethanol saturated with dry hydrochloride gas and resulting solution was refluxed for six hours. Reaction mixture was evaporated in reduced pressure and resulting pale yellow oil was dissolved in 300 ml of ethanol saturated with dry ammonia gas. The solution was kept to stand at room temperature for three days, and then evaporated in reduced pressure. Resulting solid was crystallized from benzene to give 6.5 g of the pure product as platelets.

Table 1

Compound $$\begin{array}{c} H\ H\ H\ H \\ HC-C-C-C- \\ |\ \ |\ \ H\ H \\ X\ Y \end{array} \bigg\langle\!\!\!\bigcirc\!\!\!\!\!\underset{N}{\phantom{x}}\!\!\!\!\!-COZ$$

| | X | Y | Z | | LD$_{50}$(mg/kg) Intraperitoneally | Orally | ED$_{50}$(mg/kg) Intra- peritoneally | Orally |
|---|---|---|---|---|---|---|---|---|
| 1 | Br | Br | NH$_2$ | Dibromofusaric acid amine | 1167 | 1860 | 1.0 | 1.6 |
| 2 | Br | | NH$_2$ | Monobromofusaric acid amide | 633 | 1050 | 2.0 | 4.0 |
| 3 | Br | Br | N(CH$_3$)$_2$ | Dibromofusaric acid dimethylamide | 304 | 500 | 3.0 | 4.0 |
| 4 | Cl | Cl | NH$_2$ | Dichlorofusaric acid amide | 374 | 620 | 2.0 | 4.0 |
| 5 | Cl | Cl | N(CH$_3$)$_2$ | Dichlorofusaric acid dimethylamide | 188 | 300 | 5.0 | 1.6 |
| 6 | Br | Br | OH | Dibromofusaric acid | 132 | 180 | 3.2 | 4.0 |
| 7 | — | — | OH | Fusaric acid | 110 | 130 | 3.5 | 4.0 |

Having generally described the invention, a more complete understanding can be attained by reference to certain specific examples which are provided herein for purposes of illustration only and are not intended to be construed as limiting unless otherwise so specified. In Examples, 10,11-dihalofusaric acid amide is referred to as 5-(3,4-dihalobutyl) picolinamide and 10,11-dihalofusaric acid dialkylamide is referred to as N,N-dialkyl-5-(3,4-dihalobutyl) picolinamide.

| | |
|---|---|
| m.p. | 138 – 140°C |
| IR(KBr); | 1680, 1660 cm$^{-1}$ |
| UV; | $\lambda_{max}^{MeOH}$ 269 nm ($\epsilon$ 5350) |
| TLC; | Rf 0.72 (Silicagel; chloroform-methanol-acetic acid = 45:4:1) |

[EXAMPLE 3]

5-(3,4-Dichlorobutyl)picolinamide → 10,11-dichlorofusaric acid amide 10 g of 5-(3,4-dichlorobutyl)picolinic acid was added to the solution of thionyl chloride (30 ml) and chloroform (100 ml), and resulting solution was refluxed for fifteen minutes. The reaction mixture was evaporated in reduced pressure to obtain oily residue. This was dissolved in 100 ml of benzene and treated with 28% aqueous ammonia (50 ml) at 4° – 10°C with vigorous stirring for an hour. Benzene extract was evaporated in reduced pressure to give crude product as solid.

By recrystallization from benzene- n hexane, 6.5 g of the pure product as needles was yielded

| m.p. | 115 – 117°C |
|---|---|
| Anal.; | $C_{10}H_{12}ON_2Cl_2$ |
| | calc.; C 48.60, H 4.89, N 11.34, Cl 28.69 |
| | found; C 48.82, H 4.83, N 11.54, Cl 28.25 |
| IR(KBr); | 1680, 1650 cm$^{-1}$ |
| UV; | $\lambda_{max}^{MeOH}$ 268 nm ($\epsilon$ 5370) |
| TLC; | Rf 0.78 (Silicagel; benzene-pyridine-acetic acid = 30:5:1) |
| Solubility; | Soluble in methanol, acetone, benzene, chloroform; Insoluble in water, ether. |

[EXAMPLE 4]

5-(3-Bromobutyl)picolinamide → 10-mon-bromofusaric acid amide

According to the same method as Example 1 dry ammonia was reacted with acid chloride prepared from 2 g of 5-(3-bromobutyl)picolinic acid and 1.5 ml of thionyl chloride to give crude product as oil. Crude product was recrystallized from benzene-n hexane to give 1.1 g of the pure product as needles.

| m.p. | 130 – 131°C |
|---|---|
| Anal.; | $C_{10}H_{13}ON_2Br$ |
| | calc.; C 46.71, H 5.10, N 10.89, Br 31.08 |
| | found; C 46.34, H 5.32, N 10.97, Br 30.63 |
| IR(Kbr); | 1680 cm$^{-1}$ |
| UV; | $\lambda_{max}^{MeOH}$ 268 nm ($\epsilon$ 5450) |
| TLC; | Rf 0.69 (Silicagel; chloroform-methanol-acetic acid = 45:4:1) |

[EXAMPLE 5]

N-Methyl-5-(3,4-dibromobutyl)picolinamide → 10,11-dibromofusaric acid monomethylamide According to the same method as Example 1 with cooling 30% aqueous methylamine solution (100 ml) was added to the chloroform solution (200 ml) of acid chloride prepared from 10 g of 5-(3,4-dibromobutyl)-picolinic acid and 10 ml of thionyl chloride, and stirred at 8°C for an hour. Chloroform layer which was separated, was washed with 0.3% aqueous hydrochloride solution, 5% aqueous sodium bicarbonate solution, and then water. Chloroform was evaporated in reduced pressure to yield 8.7 g of crude product as oil. To purify the product, above crude product was chromatographed on silicagel using ethylacetate as developing solvent. The pure product was viscous oil and showed only one spot (Rf 0.60) on TLC (silicagel; ethylacetate, IR (liquid film) 1670 cm$^{-1}$, UV $\lambda_{max}^{MeOH}$ 268 nm.

[EXAMPLE 6]

N-Methyl-5-(3,4-dichloro butyl) picolinamide → 10,11-dichlorofusaric acid monomethylamide According to the same method as Example 5, from 5-(3,4-dichlorobutyl)picolinic acid (10 g), crude product (8.2 g) as oil was obtained The pure product which was purified by silicagel chromatography using ethylacetate as developing solvent, was viscous oil and showed only one spot (Rf 0.58) on TLC (silicagel, ethylacetate), IR (liquid film) 1670 cm$^{-1}$, UV $\lambda_{max}^{MeOH}$ 268 nm.

[EXAMPLE 7]

N.N-Dimethyl-5-(3,4-dibromobutyl)picolinamide → 10,11-dibromofusaric acid dimethylamide According to the same method as Example 5 using 40% aqueous dimethylamine solution in place of 30% aqueous methylamine solution, 8.6 g of crude product as oil was obtained. The pure product which was purified by the same method as Example 5, was viscous oil and showed only one spot (Rf 0.33) on TLC (silicagel, ethylacetate), IR (liquid film) 1630 cm$^{-1}$, UV $\lambda_{max}^{MeOH}$ 268 nm.

[EXAMPLE 8]

N.N-Dimethyl-5-(3,4-dichlorobutyl)picolinamide → 10,11-dichlorofusaric acid dimethylamide According to the same method as Example 6 using 40% aqueous dimethylamine solution in place of 30% aqueous methylamine solution, 8.5 g of crude product as oil was obtained. The pure product which was purified by the same method as Example 6, was viscous oil and showed only one spot (Rf 0.79) on TLC (silicagel; benzene-pyridine-acetic acid = 30 : 50 : 1), IR (liquid film) 1630 cm$^{-1}$, UV $\lambda_{max}^{MeOH}$ 268 nm.

We claim:

1. A halo-fusaric acid amide of the formula:

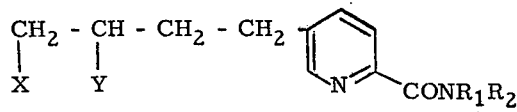

wherein X represents hydrogen or halogen; Y represents halogen; and $R_1$ and $R_2$ are same or different and represent hydrogen or a lower alkyl group.

2. A halo-fusaric acid amide according to claim 1, which is 10,11-dibromofusaric acid amide,
10,11-dichlorofusaric acid amide,
10-monobromofusaric acid amide,
10,11-dibromofusaric acid monomethylamide,
10,11-dichlorofusaric acid monomethylamide,
10,11-dibromofusaric acid dimethylamide or
10,11-dichlorofusaric acid dimethylamide.

* * * * *

UNITED STATES PATENT AND TRADEMARK OFFICE
CERTIFICATE OF CORRECTION

PATENT NO. : 3,935,221
DATED : January 27, 1976
INVENTOR(S) : TETSUJI MIYAMO ET AL It is certified that error appears in the above-identified patent and that said Letters Patent are hereby corrected as shown below:

Page 1, the designation of assignees should read as follows:

[73] Assignee: Banyu Pharmaceutical Co., Ltd., Tokyo Japan; and Hiroyoshi Hidaka, Nagoya, Japan Signed and Sealed this eighth Day of June 1976

[SEAL]

Attest:

RUTH C. MASON
Attesting Officer

C. MARSHALL DANN
Commissioner of Patents and Trademarks